United States Patent
Nakasone et al.

(10) Patent No.: US 11,408,010 B2
(45) Date of Patent: Aug. 9, 2022

(54) MUTANT-TYPE FLOWERING-INDUCING GENE, TRANSFORMED PLANT HAVING THE MUTANT-TYPE FLOWERING-INDUCING GENE, AND FLOWERING REGULATION METHOD USING THE MUTANT-TYPE FLOWERING-INDUCING GENE

(71) Applicant: Toyota Jidosha Kabushiki Kaisha, Toyota (JP)

(72) Inventors: Akari Nakasone, Miyoshi (JP); Yasuyo Shimamoto, Nagakute (JP); Madoka Abe, Nagoya (JP); Satoshi Kondo, Miyoshi (JP); Sumire Fujiwara, Tsukuba (JP); Tomoko Niki, Tsukuba (JP); Kaoru Suzuki, Sapporo (JP); Nobutaka Mitsuda, Tsukuba (JP); Yoshimi Nakano, Tsukuba (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 138 days.

(21) Appl. No.: 16/807,666

(22) Filed: Mar. 3, 2020

(65) Prior Publication Data

US 2020/0283486 A1  Sep. 10, 2020

(30) Foreign Application Priority Data

Mar. 5, 2019 (JP) .............................. JP2019-039746

(51) Int. Cl.
*C12N 15/82* (2006.01)
*C07K 14/415* (2006.01)

(52) U.S. Cl.
CPC .......... *C12N 15/827* (2013.01); *C07K 14/415* (2013.01)

(58) Field of Classification Search
CPC ........................... C12N 15/827; C07K 14/415
See application file for complete search history.

(56) References Cited

U.S. PATENT DOCUMENTS

| | | | |
|---|---|---|---|
| 6,225,530 B1 | 5/2001 | Weigel et al. | |
| 7,196,246 B2 | 3/2007 | Yano et al. | |
| 7,888,122 B2 | 2/2011 | Amasino et al. | |
| 8,785,724 B2 | 7/2014 | An et al. | |
| 9,512,441 B2 | 12/2016 | Nishimura et al. | |
| 2011/0257013 A1 | 10/2011 | Saijo et al. | |
| 2013/0019345 A1 | 1/2013 | Ohki et al. | |
| 2013/0081151 A1* | 3/2013 | Hong | C07K 14/415 800/276 |
| 2016/0304891 A1* | 10/2016 | Brower-Toland | C12N 15/8261 |
| 2018/0057831 A1 | 3/2018 | Fromm | |

FOREIGN PATENT DOCUMENTS

| | | | |
|---|---|---|---|
| JP | 2000-139250 A | 5/2000 | |
| JP | 2002-511270 A | 4/2002 | |
| JP | 2002-153283 A | 5/2002 | |
| JP | 2002-537768 A | 11/2002 | |
| JP | 2008-525013 A | 7/2008 | |
| JP | 5828302 B2 | 12/2015 | |
| WO | 2011/115222 A1 | 9/2011 | |

OTHER PUBLICATIONS

McClean, Types of Mutations, https://www.ndsu.edu/pubweb/~mcclean/plsc431/mutation/mutation4.htm, 1999 (Year: 1999).*
Ho Ho, Structural Features Determining Flower-Promoting Activity of *Arabidopsis* Flowering Locus T, The Plant Cell, Feb. 2014 (Year: 2014).*
Kardailshy I. et al., "Activiation Tagging of the Floral Inducer FT", Science (www.sciencemag.org), Dec. 3, 1999, vol. 286 (5446): pp. 1962-1965.
Kojima S. et al., "Hd3a, a Rice Ortholog of the *Arabidopsis* FT Gene, Promotes Transition to Flowering Downstream of Hd1 under Short-Day Conditions", Plant Cell Physiol., vol. 43(10): pp. 1096-1105 (2002).

* cited by examiner

*Primary Examiner* — Weihua Fan
*Assistant Examiner* — Brian James Sullivan
(74) *Attorney, Agent, or Firm* — Dinsmore & Shohl LLP

(57) ABSTRACT

A mutant-type flowering-inducing gene encoding a protein comprising an amino acid sequence in which tyrosine corresponding to the tyrosine at position 85 in the amino acid sequence of SEQ ID NO: 2 is substituted by a different amino acid, whereby flowering time is accelerated more slowly than conventionally known flowering-inducing genes, is provided.

9 Claims, 3 Drawing Sheets
Specification includes a Sequence Listing.

Fig.1

MUTANT-TYPE FLOWERING-INDUCING GENE, TRANSFORMED PLANT HAVING THE MUTANT-TYPE FLOWERING-INDUCING GENE, AND FLOWERING REGULATION METHOD USING THE MUTANT-TYPE FLOWERING-INDUCING GENE

CROSS REFERENCE TO RELATED APPLICATIONS

The present application claims priority from Japanese patent application JP 2019-039746 filed on Mar. 5, 2019, the content of which is hereby incorporated by reference into this application.

BACKGROUND

Technical Field

The present disclosure relates to a mutant-type flowering-inducing gene having a certain substitution mutation, a transformed plant that has acquired improved properties by introducing the mutant-type flowering-inducing gene thereinto, and a flowering regulation method using the mutant-type flowering-inducing gene.

Background Art

Conventionally, cross breeding of plants has been carried out with a combination based on experience and intuition, and a large number of progeny lines has been selected by comprehensive evaluation. Usually, in order to carry out crossing, it is necessary to go through a process of flowering induction, blooming/pollination, and seed setting promotion/seed harvesting. Depending on the plant type, this process can be scheduled only once a year, even in an area suitable for cultivation. Therefore, it took a very long time to develop one cultivar. Furthermore, when the cultivar to be bred was a cultivar that is difficult to flower or when the cultivars to be bred did not match in terms of time of blooming, it was very difficult to carry out desired crossing.

As explained above, in cross breeding, it was desired to develop a technology that would speed up the time of blooming by controlling the blooming of plants. It has been reported that it was possible to induce flowering (heading) of *Arabidopsis thaliana* or rice by causing a flowering-inducing gene such as the FT gene (AtFT gene) or the Hd3a gene (OsHd3a gene) to be overexpressed (JP 2000-139250 A, JP 2002-511270 A, and JP 2002-153283 A; Kardailsky I. et al., Science. 1999 Dec. 3; 286(5446):1962-5 and Kojima S. et al., Plant Cell Physiol 2002 October; 43(10):1096-105).

Meanwhile, in the case of using these flowering-inducing genes, as the genes have very powerful ability to induce flowering, flowering occurs at a stage when a plant is still small, and thus, the amount of seeds that can be harvested decreases, which has been problematic. JP 2008-525013 A and JP 2002-537768 A disclose a technology that controls the flowering time using a gene encoding a regulatory factor for controlling the expression of the flowering-inducing gene. However, as the technology disclosed in JP 2008-525013 A and JP 2002-537768 A causes the introduced regulatory factor to affect genes other than the flowering-inducing gene, undesirable characteristics may be imparted.

In addition, JP Patent No. 5828302 discloses a technology related to sugarcane into which the rice flowering-inducing gene Hd3a has been introduced to change the flowering time. However, even the technology disclosed in JP Patent No. 5828302 is also problematic because as the gene has very powerful ability to induce flowering, flowering occurs at a stage when a plant is still small.

Further, US2018/0057831 A1 discloses a technology that regulates the flowering time by allowing the expression of a flowering-inducing gene downstream of an alcohol-induced promoter. However, according to the technology disclosed in US2018/0057831 A1, the promoter needs to be activated with the aid of alcohol, which causes a problem that flowering regulation is time- and cost-consuming. Furthermore, WO2011/115222 A1 discloses a technology that regulates the flowering time by introducing a mutation into a certain site of the protein encoded by the Hd3a gene of rice so as to promote or suppress the formation of a florigen activation complex. However, according to the technology disclosed in WO2011/115222 A1, it is necessary to examine the structural stability of overall factors constituting a florigen activation complex, and therefore, the technology cannot be a simplified method. Moreover, US2011/0257013 A1 discloses a technology that regulates the flowering time by allowing the expression of a flowering-inducing gene downstream of a copper ion-inducible promoter. However, according to the technology disclosed in US2011/0257013 A1, the promoter needs to be activated with the aid of the copper ion-inducible promoter, which causes a problem that flowering regulation is time- and cost-consuming.

SUMMARY

As described above, flowering of a plant cannot be regulated at the desired time even by simply introducing a flowering-inducing gene into the plant. The flowering time can be regulated only by a method using an inducible promoter for regulating the expression of a flowering-inducing gene or modifying a complicated florigen activation complex, which has been problematic.

In consideration of the above-described circumstances, the present disclosure provides a transformed plant having a novel mutant-type flowering-inducing gene introduced thereinto, the gene having ability to induce flowering so as to function for accelerating the flowering time more slowly than conventionally known flowering-inducing genes, and a flowering regulation method using the mutant-type flowering-inducing gene.

For example, introducing a flowering-inducing gene having a certain substitution mutation makes it possible to induce flowering more slowly than when a conventionally known wild-type flowering-inducing gene is introduced.

(1) A mutant-type flowering-inducing gene encoding a protein comprising an amino acid sequence in which tyrosine corresponding to tyrosine at position 85 in the amino acid sequence of SEQ ID NO: 2 is substituted by a different amino acid.

(2) The mutant-type flowering-inducing gene according to (1), wherein the different amino acid is asparagine.

(3) The mutant-type flowering-inducing gene according to (1), which encodes the following protein (a) or (b):

(a) a protein comprising the amino acid sequence of SEQ ID NO: 4; or (b) a protein having ability to induce flowering, comprising an amino acid sequence having 90% or more identity to the amino acid sequence of SEQ ID NO: 4, wherein an amino acid corresponding the 85th amino acid in the amino acid sequence of SEQ ID NO: 4 is asparagine.

(4) The mutant-type flowering-inducing gene according to (1), which encodes the following protein (c) or (d):

(c) a protein comprising the amino acid sequence of SEQ ID NO: 6; or (d) a protein having ability to induce flowering, comprising an amino acid sequence having 90% or more identity to the amino acid sequence of SEQ ID NO: 6, wherein an amino acid corresponding to the 87th amino acid in the amino acid sequence of SEQ ID NO: 6 is asparagine.

(5) A transformed plant or transformed plant cell, wherein the mutant-type flowering-inducing gene according to any one of (1) to (4) has been introduced thereinto.

(6) The transformed plant or transformed plant cell according to (5), which belongs to the family Poaceae.

(7) The transformed plant or transformed plant cell according to (5), which belongs to the genus *Saccharum, Erianthus, Sorghum*, or *Miscanthus*.

(8) A flowering induction method, comprising introducing the mutant-type flowering-inducing gene according to any one of (1) to (4).

(9) The flowering induction method according to (8), which comprises introducing the mutant-type flowering-inducing gene into a plant belonging to the family Poaceae.

(10) The flowering induction method according to (8), which comprises introducing the mutant-type flowering-inducing gene into a plant belonging to the genus *Saccharum, Erianthus, Sorghum*, or *Miscanthus*.

Using the mutant-type flowering-inducing gene according to the present disclosure, which is a mutant-type flowering-inducing gene having a certain substitution mutation, makes it possible to promote flowering more slowly than when a conventionally known wild-type flowering-inducing gene is introduced. Therefore, in the case of the transformed plant or transformed plant cell according to the present disclosure, flowering induction occurs at a stage when a plant has grown more largely than when a conventionally known flowering-inducing gene is introduced. Accordingly, the transformed plant or transformed plant cell according to the present disclosure has an improved feature that the flowering time is accelerated while ensuring a sufficient seed yield.

BRIEF DESCRIPTION OF THE DRAWINGS

FIG. 1 shows the multiple alignment of amino acid sequences encoded by various plant-derived flowering-inducing genes; ZmZCN8 corresponds to an amino acid sequence encoded by a corn-derived flowering-inducing gene (SEQ ID NO: 7); GmFT5a corresponds to an amino acid sequence encoded by a soybean-derived flowering-inducing gene (SEQ ID NO: 8); AtFT corresponds to an amino acid sequence encoded by a *Arabidopsis thaliana*-derived flowering-inducing gene (SEQ ID NO: 9); AtTSF corresponds to an amino acid sequence encoded by an *Arabidopsis thaliana*-derived flowering-inducing gene (SEQ ID NO: 10); GmFT2a corresponds to an amino acid sequence encoded by a soybean-derived flowering-inducing gene (SEQ ID NO: 11); SlSFT corresponds to an amino acid sequence encoded by a tomato-derived flowering-inducing gene (SEQ ID NO: 12); OsHd3a corresponds to an amino acid sequence encoded by a rice-derived flowering-inducing gene (SEQ ID NO: 13); and MdFT1 corresponds to an amino acid sequence encoded by an apple-derived flowering-inducing gene (SEQ ID NO: 14) (the string of letters and numbers that follows each gene notation is the GenBank accession number for each gene).

DETAILED DESCRIPTION

Figure 2:
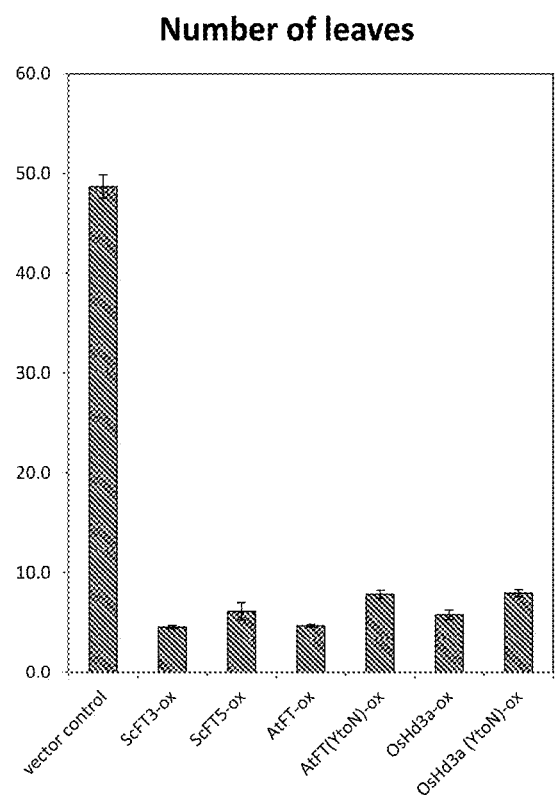
FIG. 2 is a characteristic diagram showing the results of investigating flower bud formation when transformed plants prepared by separately introducing mutant-type FT genes into the FT function-deficient strain were cultivated under long-day conditions.

The present disclosure will be described in detail below.

According to the present disclosure, a mutant-type flowering-inducing gene having a certain substitution mutation is introduced into a plant cell to serve as a host. Accordingly, flowering induction occurs in the transformed plant having the mutant-type flowering-inducing gene introduced thereinto earlier than flowering induction in a wild-type plant not introducing the mutant-type flowering-inducing gene. Meanwhile, flowering induction occurs in the transformed plant later than flowering induction in a transformed plant having a conventionally known wild-type flowering-inducing gene introduced thereinto or showing enhanced expression of the conventionally known flowering-inducing gene present as an endogenous gene. In the following explanation, a phenomenon in which flowering induction occurs earlier than flowering induction in a wild-type plant, but later than flowering induction in a transformed plant having a conventionally known wild-type flowering-inducing gene introduced thereinto or showing enhanced expression of the conventionally known flowering-inducing gene present as an endogenous gene is expressed as, for example, "slow flowering induction" or "flowering induction occurs slowly."

The term "flowering induction" used herein refers to transition from the vegetative growth phase to the reproductive growth phase, which means formation, differentiation, and development of flower buds that occur before blooming. In addition, flowering is induced as a result of increased expression of various related genes caused by the formation of a complex of a florigen transported to the shoot apex through the vascular phloem. Therefore, the flowering induction time can also be judged by observing the formation, differentiation, and development of flower buds, by detecting the presence of a florigen or a florigen activation complex or by detecting the transcript of a gene which is increasingly expressed by the florigen activation complex.

Mutant-Type Flowering-Inducing Genes Involved in Slow Flowering Induction

The mutant-type flowering-inducing gene according to the present disclosure is a gene encoding a mutant-type flowering-inducing protein in which a specific amino acid residue is substituted by a different amino acid. The specific amino acid residue specified herein is a tyrosine residue at a specific position preserved in various plant-derived flowering-inducing genes. In one example, an amino acid residue to be substituted is a tyrosine residue at position 85 in the *Arabidopsis thaliana*-derived flowering-inducing gene (NCBI Accession No. NM_105222) as the standard gene. The nucleotide sequence of the coding region in the *Arabidopsis thaliana*-derived flowering-inducing gene (NCBI Accession No. NM_105222) is shown in SEQ ID NO:1, and the amino acid sequence of the protein encoded by the flowering-inducing gene is shown in SEQ ID NO: 2. Specifically, the tyrosine residue to be substituted is located at position 85 from the N terminus of the amino acid sequence of SEQ ID NO: 2.

Although the amino acid residue (tyrosine residue) to be substituted is located at position 85 in the protein encoded by the flowering-inducing gene derived from *Arabidopsis thaliana*, the position will be numerically different in proteins encoded by plant-derived flowering-inducing genes other than *Arabidopsis*. For example, in the case of a rice-derived flowering-inducing gene (referred to as "OsHd3a gene"), the tyrosine residue to be substituted is located at position 87. Thus, the tyrosine to be substituted can be defined as corresponding to tyrosine at position 85 in the protein encoded by the *Arabidopsis thaliana*-derived flowering-inducing gene.

Figure 1:
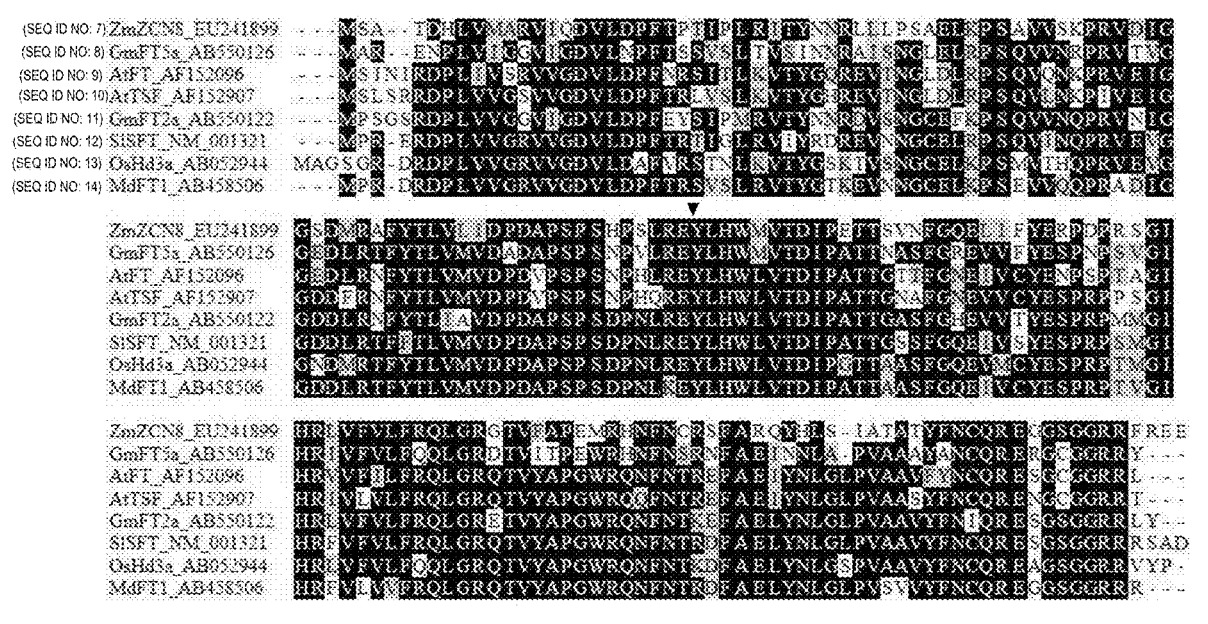

Specifically, tyrosine residue to be substituted can be identified based on the amino acid sequence of SEQ ID NO: 2 in proteins encoded by various plant-derived flowering-inducing genes. For example, as shown in FIG. 1, by creating the multiple alignment of amino acid sequences encoded by various plant-derived flowering-inducing genes, the tyrosine residue to be substituted (the tyrosine residue with a triangle mark in FIG. 1) can be identified in each amino acid sequence. In FIG. 1, ZmZCN8 corresponds to an amino acid sequence encoded by a corn-derived flowering-inducing gene (SEQ ID NO: 7), GmFT5a corresponds to an amino acid sequence encoded by a soybean-derived flowering-inducing gene (SEQ ID NO: 8), AtFT corresponds to an amino acid sequence encoded by a *Arabidopsis thaliana*-derived flowering-inducing gene (SEQ ID NO: 9), AtTSF corresponds to an amino acid sequence encoded by an *Arabidopsis thaliana*-derived flowering-inducing gene (SEQ ID NO: 10), GmFT2a corresponds to an amino acid sequence encoded by a soybean-derived flowering-inducing gene (SEQ ID NO: 11), SlSFT corresponds to an amino acid sequence encoded by a tomato-derived flowering-inducing gene (SEQ ID NO: 12), OsHd3a corresponds to an amino acid sequence encoded by a rice-derived flowering-inducing gene (SEQ ID NO: 13), and MdFT1 corresponds to an amino acid sequence encoded by an apple-derived flowering-inducing gene (SEQ ID NO: 14). In FIG. 1, the string of letters and numbers that follows each gene notation is the GenBank accession number for each gene.

The thus identified tyrosine residue to be substituted may be substituted by glutamine or asparagine having an amide group in some embodiments and by asparagine in particular embodiments. More specifically, an amino acid sequence in which the tyrosine residue to be substituted in the amino acid sequence of SEQ ID NO: 2 encoded by the *Arabidopsis thaliana*-derived flowering-inducing gene is substituted by asparagine is shown in SEQ ID NO: 4. The nucleotide sequence encoding the amino acid sequence of SEQ ID NO: 4 is shown in SEQ ID NO: 3. An amino acid sequence in which the tyrosine residue to be substituted in the amino acid sequence encoded by the rice-derived flowering-inducing gene (OsHd3a gene) is substituted by asparagine is shown in SEQ ID NO: 6. The nucleotide sequence encoding the amino acid sequence of SEQ ID NO: 6 is shown in SEQ ID NO: 5.

In other words, the mutant-type flowering-inducing gene according to the present disclosure is, for example, a gene encoding a protein comprising the amino acid sequence of SEQ ID NO: 4 or 6. In addition, the mutant-type flowering-inducing gene according to the present disclosure also encompasses a mutant-type gene obtained by introducing the mutation into a gene homologous to the *Arabidopsis thaliana*- or rice-derived wild-type flowering-inducing gene. These homologous genes include both genes that have evolved and branched from a common ancestor gene and genes that simply have similar nucleotide sequences, unlike the evolved and branched genes. Genes that have evolved and branched from a common ancestor gene include homologous genes (orthologs) of two different species and homologous genes (paralogs) that are generated within one species due to duplication. Genes homologous to the above-described flowering-inducing gene can be readily searched for or identified based on the nucleotide sequence of the *Arabidopsis thaliana*- or rice-derived wild-type flowering-inducing gene or the amino acid sequence of the protein encoded by the gene using a known database such as GenBank.

Further, the mutant-type flowering-inducing gene according to the present disclosure is not limited to a gene encoding a protein comprising the amino acid sequence of SEQ ID NO: 4 or 6 and may be a gene encoding a protein comprising an amino acid sequence having 80% or more identity, 85% or more identity in some embodiments, 90% or more identity in some other embodiments, 95% or more identity in still some other embodiments, and 98% or more identity in yet some other embodiments to the amino acid sequence of SEQ ID NO: 4 or 6 and retaining the asparagine residue after substitution described above. Note that a protein having an amino acid sequence that is different from the amino acid sequence of SEQ ID NO: 4 or 6 functions to induce slow flowering induction when it is expressed in a host plant. Here, the value of identity is a value obtained with default settings using a computer program implemented with the BLAST (Basic Local Alignment Search Tool) program and a database storing gene sequence information.

Furthermore, the mutant-type flowering-inducing gene according to the present disclosure is not limited to a gene encoding a protein comprising the amino acid sequence of SEQ ID NO: 4 or 6 and may be a gene encoding a protein comprising an amino acid sequence, in which one or more amino acids are deleted, substituted, added, or inserted in the amino acid sequence of SEQ ID NO: 4 or 6 and which retains the asparagine residue after substitution described above, and functioning to cause slow flowering induction. Here, the expression "one or more amino acids" means, for example, 1 to 20 amino acids, 1 to 10 amino acids, 1 to 7 amino acids, 1 to 5 amino acids, and 1 to 3 amino acids. Amino acids can be deleted, substituted, or added by modifying a nucleotide sequence encoding a protein comprising the amino acid sequence of SEQ ID NO: 4 or 6 by a technique known in the art. A mutation can be introduced into a nucleotide sequence by a known method such as the Kunkel method or the Gapped duplex method or a method similar to such method. A mutation is introduced using, for example, a mutagenesis kit (e.g., Mutant-K or Mutant-G (trade name, TAKARA Bio Inc.)) or an LA PCR in vitro Mutagenesis series kit (trade name, TAKARA Bio Inc.) by the site-directed mutagenesis method. Mutagenesis may be carried out by a method using a chemical mutation agent such as EMS (ethyl methanesulfonic acid), 5-bromouracil, 2-aminopurine, hydroxylamine, N-methyl-N'-nitro-N-nitrosoguanidine, and a different carcinogenic compound or a method involving radiation treatment or ultraviolet treatment typically with X-ray, alpha ray, beta ray, gamma ray, or ion beam.

Moreover, the mutant-type flowering-inducing gene according to the present disclosure may be a gene encoding a protein hybridizing with all or part of a complementary strand of DNA comprising the nucleotide sequence of SEQ ID NO: 3 or 5 under stringent conditions, functioning to cause slow flowering induction, and comprising the amino acid sequence retaining the asparagine residue after substitution described above. The term "stringent conditions" used herein refers to conditions under which so-called specific hybrids are formed while non-specific hybrids are not formed. For example, such conditions include hybridization at 45° C. with 6×SSC (sodium chloride/sodium citrate) and subsequent washing at 50° C. to 65° C. with 0.2 to 1×SSC and 0.1% SDS or hybridization at 65° C. to 70° C. with 1×SSC and subsequent washing at 65° C. to 70° C. with 0.3×SSC. Hybridization can be carried out by a conventionally known method such as the method described in J. Sambrook et al. Molecular Cloning, A Laboratory Manual, 2nd Ed., Cold Spring Harbor Laboratory (1989).

Similarly, it is also possible to introduce a mutation encoding the amino acid sequence, in which the tyrosine residue to be substituted is substituted by asparagine, into the various plant-derived wild-type flowering-inducing genes shown in FIG. 1. Specifically, it is possible to prepare these various plant-derived mutant-type flowering-inducing genes by introducing a mutation encoding an amino acid sequence in which the tyrosine residue at position 83 in the amino acid sequence (SEQ ID NO: 7) encoded by the corn-derived flowering-inducing gene (ZmZCN8), the tyrosine residue at position 83 in the amino acid sequence (SEQ ID NO: 8) encoded by the soybean-derived flowering-inducing gene (GmFT5a), the tyrosine residue at position 85 in the amino acid sequence (SEQ ID NO: 10) encoded by the *Arabidopsis thaliana*-derived flowering-inducing gene (AtTSF), the tyrosine residue at position 85 in the amino acid sequence (SEQ ID NO: 11) encoded by the soybean-derived flowering-inducing gene (GmFT2a), the tyrosine residue at position 84 in the amino acid sequence (SEQ ID NO: 12) encoded by the tomato-derived flowering-inducing gene (SISFT), or the tyrosine residue at position 84 in the amino acid sequence (SEQ ID NO: 14) encoded by the apple-derived flowering-inducing gene (MdFT1) is substituted by asparagine.

Further, the mutant-type flowering-inducing gene according to the present disclosure is not limited to a gene encoding an amino acid sequences having a substitution mutation based on the amino acid sequence of any one of SEQ ID NOS: 7, 8, 10 to 12, and 14 and may be a gene encoding a protein comprising an amino acid sequence having 80% or more identity, 85% or more identity in some embodiments, 90% or more identity in some other embodiments, 95% or more identity in still some other embodiments, and 98% or more identity in yet some other embodiments to the amino acid sequence and retaining the asparagine residue after substitution described above. Note that a protein comprising an amino acid sequence retaining the asparagine residue after substitution functions to cause slow flowering induction when it is expressed in a host plant.

Furthermore, the mutant-type flowering-inducing gene according to the present disclosure is not limited to a gene encoding an amino acid sequences having a substitution mutation based on the amino acid sequence of any one of SEQ ID NOS: 7, 8, 10 to 12, and 14 and may be a gene encoding a protein comprising an amino acid sequence, in which one or more amino acids are deleted, substituted, added, or inserted in the amino acid sequence and which retains the asparagine residue after substitution described above, and functioning to cause slow flowering induction. Here, the expression "one or more amino acids" means, for example, 1 to 20 amino acids, 1 to 10 amino acids in some embodiments, 1 to 7 amino acids in some other embodiments, 1 to 5 amino acids in still some other embodiments, and 1 to 3 amino acids in some particular embodiments. Note that a protein comprising an amino acid sequence retaining the asparagine residue after substitution functions to cause slow flowering induction when it is expressed in a host plant.

Expression Vector

An expression vector is constructed such that it includes a nucleic acid having a promoter nucleotide sequence that enables constitutive expression and the above-described mutant-type flowering-inducing gene. It is possible to produce a transformed plant having the mutant-type flowering-inducing gene introduced thereinto with the use of the expression vector.

Various conventionally known vectors can be used herein as a base vector for the expression vector. For example, a plasmid, phage, cosmid, or the like can be used, and a vector can be appropriately selected according to a plant cell into which the vector is introduced and a method for introducing the vector. Specific examples of such vector include pBI vectors such as pBR322, pBR325, pUC19, pUC119, pBluescript, and pBluescriptSK. In particular, in a case in which the method for introducing the vector into a plant cell uses *Agrobacterium*, a pBI binary vector is used in some embodiments. Specific examples of a pBI binary vector include pBIG, pBIN19, pBI101, pBI121, and pBI221.

The promoter is not particularly limited as long as it is a promoter that allows the mutant-type flowering-inducing gene to be expressed in a plant, and a known promoter can be used as appropriate. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase/oxidase small subunit gene promoter, a napin gene promoter, and an oleosin gene promoter. Of these, a cauliflower mosaic virus 35S promoter, an actin gene promoter, or an ubiquitin gene promoter is used in some embodiments. The use of each of the above-described promoters allows an arbitrary gene to be strongly expressed when the gene is introduced into a plant cell.

In addition, a promoter that functions to allow a nucleic acid to be expressed in a plant in a site-specific manner can also be used. Any conventionally known promoter can be used as such promoter. By introducing the mutant-type flowering-inducing gene in a site-specific manner using such promoter, it is possible to induce expression of the gene in a plant organ or plant tissue formed with cells having the mutant-type flowering-inducing gene introduced thereinto so as to cause slow flowering induction.

The expression vector may further include a nucleic acid having a different segment sequence, in addition to a promoter and the mutant-type flowering-inducing gene. The nucleic acid having a different segment sequence is not particularly limited. Examples thereof include a nucleic acid having a terminator nucleotide sequence, a nucleic acid having a transformant selection marker nucleotide sequence, a nucleic acid having an enhancer nucleotide sequence, and a nucleic acid having a nucleotide sequence for improving translation efficiency. In addition, the recombinant expression vector may further have a T-DNA region. A T-DNA region can improve the efficiency of nucleic acid introduction especially when introducing a nucleic acid having a nucleotide sequence in the recombinant expression vector into a plant cell using *Agrobacterium*.

The nucleic acid having a terminator nucleotide sequence is not particularly limited as long as it functions as a transcription termination site, and it may be a known nucleic acid. For example, specific examples of such nucleic acid that can be used include the transcription termination site of the nopaline synthase gene (Nos terminator) and the transcription termination site of cauliflower mosaic virus 35S (CaMV35S terminator). Of these, the Nos terminator is used in some embodiments. The above-described recombinant vector can be prevented from causing an event of, for example, synthesizing an unnecessarily long transcript after being introduced into a plant cell by placing the terminator at an appropriate site.

Examples of the nucleic acid having a transformant selection marker nucleotide sequence that can be used include nucleic acids having drug-resistant genes. Specific examples of such drug-resistant genes include drug resistant genes against, for example, hygromycin, bleomycin, kanamycin, gentamicin, and chloramphenicol. Accordingly, by selecting a plant that grows in a medium containing such antibiotics, a transformed plant can be readily selected.

Examples of the nucleic acid having a nucleotide sequence for improving translation efficiency include a nucleic acid having the tobacco mosaic virus-derived omega sequence. The expression efficiency of the above-described flowering-inducing gene can be increased by placing this omega sequence-containing nucleic acid in the untranslated region (5'UTR) upstream of the protein coding region. Thus, the above-described recombinant expression vector can contain nucleic acids having various DNA segment sequences depending on the purpose.

The method for constructing a recombinant expression vector is also not particularly limited. A nucleic acid having the above-described promoter nucleotide sequence, the above-described mutant-type flowering-inducing gene, and if needed, a nucleic acid having the above-described other DNA segment sequences can be inserted into an appropriately selected vector to serve as a base in a certain order. For example, the mutant-type flowering-inducing gene and a nucleic acid having a promoter nucleotide sequence (and if needed, for example, a nucleic acid having a terminator nucleotide sequence) are ligated, thereby inserting the ligation product into the vector.

In addition, a method for propagating (producing) the expression vector is also not particularly limited, and a conventionally known method can be used. Usually, the vector can be propagated in *Escherichia coli* used as a host. At such time, the type of *Escherichia coli* may be selected depending on the vector type in some embodiments.

Transformation

The expression vector is introduced into a plant cell of interest by an ordinary transformation method. The method for introducing the expression vector into a plant cell (transformation method) is not particularly limited, and an appropriate conventionally known method can be used depending on the plant cell. Specifically, for example, a method using *Agrobacterium* or a method in which the expression vector is directly introduced into a plant cell can be used. The method using *Agrobacterium* that can be used is, for example, the method described in Bechtold, E., Ellis, J. and Pelletier, G. (1993) In Planta *Agrobacterium*-mediated gene transfer by infiltration of adult *Arabidopsis* plants. C. R. Acad. Sci. Paris Sci. Vie, 316, 1194-1199 or the method described in Zyprian E, Kado Cl, *Agrobacterium*-mediated plant transformation by novel mini-T vectors in conjunction with a high-copy vir region helper plasmid. Plant Molecular Biology, 1990, 15(2), 245-256.

Examples of the method in which the expression vector is directly introduced into a plant cell that can be used include a microinjection method, an electroporation method (electroporation method), a polyethylene glycol method, a particle gun method, a protoplast fusion method, and a calcium phosphate method.

In addition, when the method in which the mutant-type flowering-inducing gene is directly introduced into a plant cell is employed, a nucleic acid having a transcription unit such as a promoter nucleotide sequence or a nucleic acid having a transcription terminator nucleotide sequence, which is required for the expression of a mutant-type flowering-inducing gene of interest, and a mutant-type flowering-inducing gene of interest are necessary and sufficient, and the vector function is not necessary. Further, even a nucleic acid consisting of the protein coding region of the mutant-type flowering-inducing gene without having a transcription unit is acceptable as long as it can be integrated into a transcription unit of the host genome, thereby expressing the gene of interest. Even in a case in which the nucleic acid cannot be integrated into the host genome, it is acceptable as long as the mutant-type flowering-inducing gene is transcribed and/or translated in the cell.

Examples of plant cells into which the expression vector or a mutant-type flowering-inducing gene of interest without the expression vector is introduced include cells, callus, and suspension culture cells of tissues in plant organs such as flowers, leaves, and roots. The expression vector described herein may be appropriately constructed as a vector suitable for the type of a plant to be produced or it may be constructed as a versatile expression vector and then introduced into a plant cell.

A plant formed with cells into which an expression vector is introduced is not particularly limited. In other words, it is possible to cause slow flowering induction in any plant by introducing the above-described mutant-type flowering-inducing gene. A target plant is, for example, a flowering plant, and an angiosperm among flowering plants. Examples of target angiosperms include dicotyledonous plants and monocotyledonous plants such as plants belonging to the families Brassicaceae, Poaceae, Solanaceae, Leguminosae, and Salicaceae (see below), but are not limited to these plants.

Family Brassicaceae: thale-cress (*Arabidopsis thaliana*), lyrate rockcress (*Arabidopsis lyrata*), rapes (*Brassica rapa, Brassica napus, Brassica campestris*), cabbage (*Brassica oleracea* var. *capitata*), napa (*Brassica rapa* var. *pekinensis*), ging-geng-cai (*Brassica rapa* var. *chinensis*), turnip (*Brassica rapa* var. *rapa*), Nozawana (*Brassica rapa* var. *hakabura*), Mizuna (*Brassica rapa* var. *laciniifolia*), Komatsuna (*Brassica rapa* var. *perviridis*), pak choy leaves (*Brassica rapa* var. *chinensis*), radish (*Raphanus sativus*), wasabi or Japanese-horseradish (*Wasabia japonica*), pink shepherd's-purse (*Capsella rubella*), and the like Family Chenopodiaceae: beet (*Beta vulgaris*)

Family Aceraceae: sugar maple (*Acer saccharum*)

Family Euphorbiaceae: castor bean (*Ricinus communis*)

Family Solanaceae: tobacco (*Nicotiana tabacum*), eggplant (*Solanum melongena*), potato (*Solanum tuberosum*), tomato (*Solanum lycopersicum*), pepper (*Capsicum annuum*), petunia (*Petunia hybrida*), and the like Family Leguminosae: soybean (*Glycine max*), garden pea (*Pisum sativum*), broad bean (*Vicia faba*), Japanese wisteria (*Wisteria floribunda*), peanut (*Arachis hypogaea*), birdsfoot trefoil (*Lotus japonicus*), kidney bean (*Phaseolus vulgaris*), adzuki bean or English red mung bean (*Vigna angularis*), acacia (*Acacia*), barrelclover (*Medicago truncatula*), chickpea (*Cicer arietinum*), and the like Family Asteraceae: Chrysanthemum (*Chrysanthemum morifolium*), sunflower (*Helianthus annuus*), and the like Family Arecaceae: oil palm (*Elaeis guineensis, Elaeis oleifera*), coconut palm (*Cocos nucifera*), date palm (*Phoenix dactylifera*), wax palm (*Copernicia*), and the like Family Anacardiaceae: wax tree (*Rhus succedanea*), cashew tree (*Anacardium occidentale*), lacquer tree (*Toxicodendron vernicifluum*), mango (*Mangifera indica*), pistachio (*Pistacia vera*), and the like Family Cucurbitaceae: squash (*Cucurbita maxima, Cucurbita moschata, Cucurbita pepo*), cucumber (*Cucumis sativus*), Japanese snake gourd (*Trichosanthes cucumeroides*), bottle gourd (*Lagenaria siceraria* var. *gourda*), and the like Family Rosaceae: almond (*Amygdalus communis*), rose (*Rosa*), strawberry (*Fragaria vesca*), Japanese cherry (*Prunus*), apple (*Malus pumila* var. *domestica*), peach (*Prunus persica*), and the like Family Vitaceae: grape (*Vitis vinifera*)

Family Caryophyllaceae: carnation (*Dianthus caryophyllus*) and the like

Family Salicaceae: poplar (*Populus trichocarpa, Populus nigra, Populus tremula*) and the like Family Poaceae: corn (*Zea mays*), rice (*Oryza sativa*), barley (*Hordeum vulgare*), bread wheat (*Triticum aestivum*), wild einkorn wheat (*Triticum urartu*), Tausch's goatgrass (*Aegilops tauschii*), Purple false brome (*Brachypodium distachyon*), Asian bamboo (*Phyllostachys*), sugarcane (*Saccharum officinarum*), Napier grass (*Pennisetum purpureum*), Erianthus (*Erianthus ravennae*), Japanese silver grass (*Miscanthus virgatum*), sorghum (*Sorghum bicolor*), switch grass (*Panicum*), and the like Family Liliaceae: tulip (*Tulipa*), lily (*Lilium*), and the like Of these, plants belonging to the family Poaceae such as sugarcane, corn, *Erianthus*, rice, sorghum, and bread wheat, and in particular, plants belonging to the genus *Saccharum, Erianthus, Sorghum*, or *Miscanthus* are exemplified in some embodiments.

Other Steps and Methods

After the above-described transformation treatment, a selection step for selecting an appropriate transformant from among plants can be performed by a conventionally known method. The selection method is not particularly limited. For example, selection may be carried out based on drug resistance such as hygromycin resistance. Alternatively, after growing transformants, the flowering induction time of each plant is observed, and then, a plant in which flowering induction occurs earlier than the wild-type plant but later than a transformed plant into which a conventionally known wild-type flowering-inducing gene has been introduced may be selected.

In addition, a progeny plant can be produced from a transformed plant obtained by the transformation treatment in accordance with an ordinary method. By selecting a progeny plant in which the mutant-type flowering-inducing gene is maintained based on the flowering induction time, it is possible to produce a plant line which stably maintains the feature of inducing flowering slowly because of the mutant-type flowering-inducing gene. It is also possible to obtain a plant-propagating material such as plant cells, seeds, fruits, stock, callus, tuber, cut ears, or mass from a transformed plant or a progeny thereof and produce a stable plant line having the characteristic using such material on a large scale.

As described above, according to the present disclosure, it is possible to cause slow flowering induction to occur by introducing the above-described mutant-type flowering-inducing gene into cells. In other words, flowering induction can occur in a transformed plant into which the mutant-type flowering-inducing gene has been introduced or a progeny thereof earlier than the wild-type plant while the flowering induction occurs at a stage when the plant has grown more largely than a transformed plant into which a conventionally known wild-type flowering-inducing gene has been introduced. Accordingly, the amount of seeds of the transformed plant into which the mutant-type flowering-inducing gene has been introduced or a progeny thereof does not decrease due to flowering induction at a stage when the plant is still small.

EXAMPLES

The present disclosure will be described in detail with reference to the Examples below. However, the scope of the present disclosure is not limited to the Examples.

[Preparation of Vector for *Arabidopsis thaliana* Transformation]

In the Examples, an expression vector for expressing a mutant-type *Arabidopsis thaliana*-derived flowering-inducing gene having a Y85N mutation (AtFT (YtoN) gene) and an expression vector for expressing a rice-derived mutant-type flowering-inducing gene having a Y87N mutation (OsHd3a (YtoN) gene) were prepared.

In addition, in the Examples, an expression vector for expressing the ScFT3 and ScFT5 genes was prepared using the amino acid sequence information disclosed in the previously published papers on the FT family genes in sugarcane (Coelho C P (2013) MOLECULAR REGULATORY MECHANISM OF FLORAL TRANSITION BY FT/TFL1 ORTHOLOGS AND THE AUTONOMOUSLY EXPRESSED ScID1 MONOCOT-SPECIFIC TRANSCRIPTION FACTOR IN SUGARCANE. Thesis. Universidade Federal de Lavras; and Coelho C P, Minow M A, Chalfun-Junior A, Colasanti J. (2014) Putative sugarcane FT/TFL1 genes delay flowering time and alter reproductive architecture in *Arabidopsis*. Front Plant Sci. 5:221) for comparison. In the Examples, an expression vector expressing the wild-type flowering-inducing gene (AtFT gene) derived from *Arabidopsis thaliana* and an expression vector expressing the wild-type flowering-inducing gene (OsHd3a gene) derived from rice were prepared for comparison.

Specifically, at first, DNA fragments each containing a coding sequence obtained by the method described below were obtained. Next, the obtained DNA fragments were separately incorporated into pDONR207 (Thermo Fisher Scientific) or pENTR/D-TOPO (Thermo Fisher Scientific), thereby producing entry clones. Subsequently, each DNA fragment including one coding region was incorporated into a binary vector pDEST_35S_HSP_GWB5 by LR reaction using the entry clone and LR clonase II (Thermo Fisher Scientific), thereby producing a vector for *Arabidopsis thaliana* transformation. The vector for *Arabidopsis thaliana* transformation strongly expresses the corresponding gene constantly under control of the CaMV 35S promoter and the HSP terminator in *Arabidopsis thaliana*.

pDEST_35S_HSP_GWB5 was prepared by cleaving a fragment containing attR4-ccdB-attR2-SRDX of R4pGWB5_SRDX_HSP (Oshima Y, Mitsuda N, Nakata M, Nakagawa T, Nagaya S, Kato K, Ohme-Takagi M. Novel vector systems to accelerate functional analysis of transcription factors using chimeric repressor gene-silencing technology (CRES-T) (2011) Plant Biotech. 28:201-10) by restriction enzyme HindIII treatment and inserting a fragment containing 35S-Ω-attR1-ccdB-attR2 obtained by treating pDEST35SHSP (Oshima Y, Shikata M, Koyama T, Ohtsubo N, Mitsuda N, Ohme-Takagi M. MIXTA-like transcription factors and WAX INDUCER1/SHINE1 coordinately regulate cuticle development in *Arabidopsis* and *Torenia fournieri*. (2013) Plant Cell. 25:1609-24) with HindIII into the cleavage site.

Hereinafter, detailed procedures for preparing an entry clone for each gene will be described.

<AtFT Gene>

In the Examples, a transformant that overexpresses the FT gene (AtFT gene) from *Arabidopsis thaliana* was prepared for comparison. Prior to preparing a vector for *Arabidopsis thaliana* transformation for introducing the AtFT gene, a pair of primers (ggggacaagtttgtacaaaaaagcaggcttcATGTCTATAAATATAAGAGACCCTCTTAT (SEQ ID NO: 15) and ggggaccactttgtacaagaaagctgggtAAGTCTTCTTCCTCCGCAGCCACTCTCCCT (SEQ ID NO: 16)) having sequences for adding the attB1 and attB2 sequences were designed based on the nucleotide sequence of the AtFT gene disclosed with NCBI Accession No. NM_105222. An amplified fragment (SEQ ID NO: 17) including the AtFT gene was obtained by PCR using these primers. The obtained amplified fragment was incorporated into pDONR207 (Thermo Fisher Scientific) by BP reaction using BP clonase II (Thermo Fisher Scientific), thereby preparing an entry clone for the AtFT gene.

<OsHd3a Gene>

In the Examples, a transformant that overexpresses the FT gene (OsHd3a gene) from rice was prepared for comparison. Prior to preparing a vector for *Arabidopsis thaliana* transformation for introducing the OsHd3a gene, VectorBuilder Inc. was commissioned to carry out artificial synthesis of a nucleic acid fragment (SEQ ID NO: 18) to which the attB1 sequence was added to the 5' end side of the coding sequence and the attB2 sequence was added to the 3' end side of the same based on the nucleotide sequence of the OsHd3a gene disclosed with NCBI Accession No. AB052944 and incorporation of the fragment into RI201-AN (Takara Bio Inc.). An entry clone was prepared for the OsHd3a gene by BP reaction using the obtained plasmid and pDONR207 (Thermo Fisher Scientific) using BP clonase II (Thermo Fisher Scientific).

<ScFT3 Gene>

For the ScFT3 gene, a partial fragment was obtained by degenerate PCR using degenerate primers (YTIMGIGARTAYYTICAYTGGYTIGT (SEQ ID NO: 19) and TRAARTTYTGICKCCAICCIGGIGC (SEQ ID NO: 20)), and the full-length sequence was further obtained by the Race method. In addition, the ScFT3 gene was cloned into pENTR/D-TOPO (Thermo Fisher Scientific), thereby preparing an entry clone for the ScFT3 gene. For the ScFT3 gene, the full-length sequence necessary for entry clone preparation was amplified using a pair of primers (CACCCGTCGGTGGCCCATTATTG (SEQ ID NO: 21) and TCTTATTTCACCCGGATCGAGT (SEQ ID NO: 22)). The nucleotide sequence of the amplified DNA fragment including the ScFT3 gene is shown in SEQ ID NO: 23.

<ScFT5 Gene>

For the ScFT5 gene, cloning was performed based on the nucleotide sequence information of the databases, thereby obtaining full-length sequence. For the ScFT5 gene, primers for adding the attB1 sequence to the 5' side of the sequence and the attB2 sequence to the 3' end of the same (ggggacaagtttgtacaaaaaagcaggctccATGTTCAATATGTCTAGGGACCCATTGGT (SEQ ID NO: 24) and ggggaccactttgtacaagaaagctgggtcTCACCTTATGTACCTTCTTCCACCACAGCC (SEQ ID NO: 25)) were designed. The full-length sequence necessary for preparing an entry clone including the ScFT5 gene was amplified by PCR using these primers. The nucleotide sequence of the amplified DNA fragment including the ScFT5 gene is shown in SEQ ID NO: 26.

The obtained DNA fragment was incorporated into pDONR207 (Thermo Fisher Scientific) by BP reaction, thereby preparing an entry clone for the ScFT5 gene.

<AtFT(YtoN) Gene>

For the coding sequence for substituting tyrosine at position 85 of *Arabidopsis thaliana* AtFT (NCBI Accession No. NM_105222) by asparagine, a nucleotide sequence to which the attB1 sequence was added to the 5' end side and the attB2 sequence was added to the 3' end side (SEQ ID NO: 27) was designed. VectorBuilder Inc. was commissioned to carry out artificial synthesis of the designed nucleotide sequence and incorporation of the sequence into RI201-ANN (Takara Bio Inc.). An entry clone was prepared for the AtFT(YtoN) gene by BP reaction using the obtained plasmid and pDONR207 (Thermo Fisher Scientific) using BP clonase II (Thermo Fisher Scientific).

<OsHd3a(YtoN) Gene>

For the coding sequence for substituting tyrosine at position 87 of rice OsHd3a (NCBI Accession No. AB052944) by asparagine, a nucleotide sequence to which the attB1 sequence was added to the 5' end side and the attB2 sequence was added to the 3' end side (SEQ ID NO: 28) was designed. VectorBuilder Inc. was commissioned to carry out artificial synthesis of the designed nucleotide sequence and incorporation of the sequence into RI201-ANN (Takara Bio Inc.). An entry clone was prepared for the OsHd3a (YtoN) gene by BP reaction using the obtained plasmid and pDONR207 (Thermo Fisher Scientific) using BP clonase II (Thermo Fisher Scientific).

[Functional Evaluation of the Genes in *Arabidopsis thaliana*]

For functional evaluation of the AtFT (YtoN) gene and the OsHd3a (YtoN) gene, transformation of *Arabidopsis thaliana* (*Arabidopsis*) was carried out using the above-described binary vector, thereby analyzing flowering characteristics.

[Transformation Using *Agrobacterium*]

The above-described binary vector plasmid was transformed into *Agrobacterium* (*Agrobacterium tumefaciens, Rhizobium radiobacter*) GV3101 by the electroporation method and cultured in LB medium containing 50 mg/l spectinomycin, 50 mg/l gentamicin, and 50 mg/l rifampicin. Accordingly, *Agrobacterium* transformed with the binary vector was prepared.

[Preparation of *Arabidopsis thaliana* Transformants]

The *Arabidopsis thaliana* FT function-deficient strain ft-10 (Yoo S K, Chung K S, Kim J, Lee J H, Hong S M, Yoo S J, Yoo S Y, Lee J S, Ahn J H. (2005) CONSTANS activates SUPPRESSOR OF OVEREXPRESSION OF CONSTANS 1 through FLOWERING LOCUS T to promote flowering in *Arabidopsis*. Plant Physiol. 139(2):770-778) was procured from the *Arabidopsis* Biological Resource Center (ABRC). Basically, the ft-10 strain forming buds was transformed by the floral dipping method described in Clough S J, Bent A F. (1998) Floral dip: a simplified method for *Agrobacterium*-mediated transformation of *Arabidopsis thaliana*. Plant J. 16(6):735-743. In addition, transformation was carried out using *Agrobacterium* including the binary vector pDEST_35S_HSP_GWB5 that had not been subjected to LR reaction, thereby preparing a control. In order to select transformed plants, T1 seeds obtained from the plants treated by the floral dipping method were sterilized and seeded in an MS medium containing 30 mg/l hygromycin and 250 mg/l vancomycin (Murashige T, Skoog F K (1962) A revised medium for rapid growth and bio-assays with tobacco tissue cultures. Physiol. Plant 15 (3): 473-497, including 0.5% sucrose and 0.8% agar). The medium after seeding was left at 4° C. for 3 days for low-temperature treatment, followed by cultivation at 22° C. under long-day conditions (light period of 16 hours/dark period of 8 hours). On day 15 after the start of cultivation, individuals that survived antibiotics selection were transplanted as transformed plants onto culture soil. Cultivation was continued after transplantation at 22° C. under long-day conditions (light period of 16 hours/dark period of 8 hours).

[Investigation of Flowering Time]

For the investigation of flowering time of T1 plants, transformed *Arabidopsis thaliana* individuals were cultivated at 22° C. under long-day conditions (light period of 16 hours/dark period of 8 hours), and the number of days until flower bud formation was observed and the number of leaves formed by that time (stem leaves and rosette leaves) were counted.

[Measurement of the Amount of Seeds]

The amount of seeds was measured by weighing seeds collected from each of transformed plants dried for about a month after stopping irrigation using a precision balance (Excellence Plus, Metller Toledo).

[Results]

FIG. 2 shows the results of investigating flowering time by cultivating transformed plants, in which the genes were overexpressed, using the *Arabidopsis thaliana* FT function-deficient strain ft-10 as a host under long-day conditions. As shown in FIG. 2, for the vector control strain of the FT function-deficient strain ft-10, about 50 true leaves were formed before flower bud formation was observed, and the characteristic that flower bud formation is delayed for a long period of time due to FT function deficiency was confirmed. Meanwhile, flower buds were formed in transformed plants in which the conventionally known wild-type AtFT gene or wild-type OsHd3a gene was overexpressed when about 5 true leaves were formed, indicating that the FT function was complemented by the introduced gene.

For the sugarcane-derived ScFT3 gene, it was also revealed that the gene functions to complement the FT function to induce flower bud formation at a very early stage as with the conventionally known wild-type AtFT gene and the wild-type OsHd3a gene. However, it can be evaluated that the sugarcane-derived ScFT5 gene functions to induce flower bud formation relatively slowly compared to the ScFT3 gene.

Meanwhile, flower bud formation is induced in a transformed plant that overexpresses the AtFT gene having a Y85N mutation (AtFT (YtoN) gene) and a transformed plant that overexpresses the OsHd3a gene having a Y87N mutation (OsHd3a (YtoN) gene) earlier than that in the vector control strain of the FT function-deficient strain ft-10, while flower bud formation is induced slowly, which is remarkably different from the case of using the wild-type AtFT gene and the case of using the wild-type OsHd3a gene, respectively.

Figure 3:
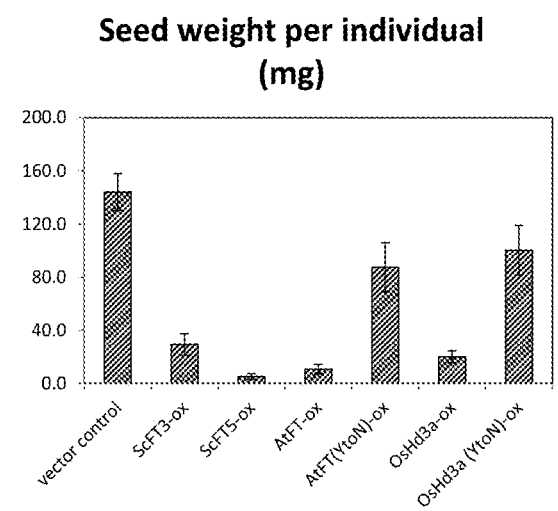
FIG. 3 is a characteristic diagram showing the results of investigating seed yield when transformed plants prepared by separately introducing mutant-type FT genes into the FT function-deficient strain were cultivated under long-day conditions.

FIG. 3 shows the results of measuring the weight of seeds per individual transformed plant for investigating the seed yields of transformed plants cultivated in the same manner. As shown in FIG. 3, it was found that a transformed plant that overexpresses the AtFT gene having a Y85N mutation (AtFT (YtoN) gene) and a transformed plant that overexpresses the OsHd3a gene having a Y87N mutation (OsHd3a (YtoN) gene) are remarkably superior to transformed plants each having any of the ScFT3 gene, the ScFT5 gene, the wild-type AtFT gene, and the wild-type OsHd3a introduced thereinto terms of seed yield.

As described above, it was shown that in the case of introducing the AtFT gene having a Y85N mutation (AtFT (YtoN) gene) or the OsHd3a gene having a Y87N mutation, flower bud formation can be induced earlier than that in the vector control strain, and the improved seed yield can be achieved.

Sequence Listing

What is claimed is:

1. A mutant Flowering Locus T (FT) gene encoding a FT protein comprising an amino acid sequence in which a tyrosine is mutated to an asparagine, wherein the tyrosine corresponds to tyrosine at position 85 in the amino acid sequence of SEQ ID NO: 2.

2. The mutant FT gene according to claim 1, which encodes the following protein (a) or (b):
   (a) a protein comprising the amino acid sequence of SEQ ID NO: 4; or
   (b) a protein having ability to induce flowering, comprising an amino acid sequence having 90% or more identity to the amino acid sequence of SEQ ID NO: 4, wherein an amino acid corresponding the 85th amino acid in the amino acid sequence of SEQ ID NO: 4 is asparagine.

3. The mutant FT gene according to claim 1, which encodes the following protein (c) or (d):
   (c) a protein comprising the amino acid sequence of SEQ ID NO: 6; or
   (d) a protein having ability to induce flowering, comprising an amino acid sequence having 90% or more identity to the amino acid sequence of SEQ ID NO: 6, wherein an amino acid corresponding to the 87th amino acid in the amino acid sequence of SEQ ID NO: 6 is asparagine.

4. A transformed plant or transformed plant cell, wherein the mutant FT gene according to claim 1 has been introduced thereinto.

5. The transformed plant or transformed plant cell according to claim 4, which belongs to the family Poaceae.

6. The transformed plant or transformed plant cell according to claim 4, which belongs to the genus *Saccharum, Erianthus, Sorghum*, or *Miscanthus*.

7. A method for inducing flower bud formation in a plant, comprising introducing to the genome of a plant the mutant FT gene according to claim 1.

8. The method according to claim 7, which comprises introducing the mutant-type flowering-inducing gene into a plant belonging to the family Poaceae.

9. The method according to claim 7, which comprises introducing the mutant-type flowering-inducing gene into a plant belonging to the genus *Saccharum, Erianthus, Sorghum*, or *Miscanthus*.

* * * * *

SEQUENCE LISTING

```
<160> NUMBER OF SEQ ID NOS: 28

<210> SEQ ID NO 1
<211> LENGTH: 528
<212> TYPE: DNA
<213> ORGANISM: Arabidopsis thaliana
<220> FEATURE:
<221> NAME/KEY: CDS
<222> LOCATION: (1)..(528)

<400> SEQUENCE: 1 atg tct ata aat ata aga gac cct ctt ata gta agc aga gtt gtt gga       48
Met Ser Ile Asn Ile Arg Asp Pro Leu Ile Val Ser Arg Val Val Gly
1               5                   10                  15 gac gtt ctt gat ccg ttt aat aga tca atc act cta aag gtt act tat       96
Asp Val Leu Asp Pro Phe Asn Arg Ser Ile Thr Leu Lys Val Thr Tyr
            20                  25                  30 ggc caa aga gag gtg act aat ggc ttg gat cta agg cct tct cag gtt      144
Gly Gln Arg Glu Val Thr Asn Gly Leu Asp Leu Arg Pro Ser Gln Val
        35                  40                  45 caa aac aag cca aga gtt gag att ggt gga gaa gac ctc agg aac ttc      192
Gln Asn Lys Pro Arg Val Glu Ile Gly Gly Glu Asp Leu Arg Asn Phe
    50                  55                  60 tat act ttg gtt atg gtg gat cca gat gtt cca agt cct agc aac cct      240
Tyr Thr Leu Val Met Val Asp Pro Asp Val Pro Ser Pro Ser Asn Pro
65                  70                  75                  80
```

-continued

```
cac ctc cga gaa tat ctc cat tgg ttg gtg act gat atc cct gct aca      288
His Leu Arg Glu Tyr Leu His Trp Leu Val Thr Asp Ile Pro Ala Thr
                 85                  90                  95 act gga aca acc ttt ggc aat gag att gtg tgt tac gaa aat cca agt      336
Thr Gly Thr Thr Phe Gly Asn Glu Ile Val Cys Tyr Glu Asn Pro Ser
            100                 105                 110 ccc act gca gga att cat cgt gtc gtg ttt ata ttg ttt cga cag ctt      384
Pro Thr Ala Gly Ile His Arg Val Val Phe Ile Leu Phe Arg Gln Leu
            115                 120                 125 ggc agg caa aca gtg tat gca cca ggg tgg cgc cag aac ttc aac act      432
Gly Arg Gln Thr Val Tyr Ala Pro Gly Trp Arg Gln Asn Phe Asn Thr
        130                 135                 140 cgc gag ttt gct gag atc tac aat ctc ggc ctt ccc gtg gcc gca gtt      480
Arg Glu Phe Ala Glu Ile Tyr Asn Leu Gly Leu Pro Val Ala Ala Val
145                 150                 155                 160 ttc tac aat tgt cag agg gag agt ggc tgc gga gga aga aga ctt tag     528
Phe Tyr Asn Cys Gln Arg Glu Ser Gly Cys Gly Gly Arg Arg Leu
                165                 170                 175

<210> SEQ ID NO 2
<211> LENGTH: 175
<212> TYPE: PRT
<213> ORGANISM: Arabidopsis thaliana

<400> SEQUENCE: 2

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 3
<211> LENGTH: 528
<212> TYPE: DNA
<213> ORGANISM: Arabidopsis thaliana
<220> FEATURE:
<221> NAME/KEY: CDS
<222> LOCATION: (1)..(528)

<400> SEQUENCE: 3 atg tct ata aat ata aga gac cct ctt ata gta agc aga gtt gtt gga      48
Met Ser Ile Asn Ile Arg Asp Pro Leu Ile Val Ser Arg Val Val Gly
1               5                   10                  15
```

```
                1               5                         10                         15
        gac gtt ctt gat ccg ttt aat aga tca atc act cta aag gtt act tat        96
        Asp Val Leu Asp Pro Phe Asn Arg Ser Ile Thr Leu Lys Val Thr Tyr
                        20                          25                  30 ggc caa aga gag gtg act aat ggc ttg gat cta agg cct tct cag gtt       144
        Gly Gln Arg Glu Val Thr Asn Gly Leu Asp Leu Arg Pro Ser Gln Val
                35                          40                  45 caa aac aag cca aga gtt gag att ggt gga gaa gac ctc agg aac ttc       192
        Gln Asn Lys Pro Arg Val Glu Ile Gly Gly Glu Asp Leu Arg Asn Phe
         50                          55                  60 tat act ttg gtt atg gtg gat cca gat gtt cca agt cct agc aac cct       240
        Tyr Thr Leu Val Met Val Asp Pro Asp Val Pro Ser Pro Ser Asn Pro
        65                   70                  75                       80 cac ctc cga gaa aac ctc cat tgg ttg gtg act gat atc cct gct aca       288
        His Leu Arg Glu Asn Leu His Trp Leu Val Thr Asp Ile Pro Ala Thr
                             85                  90                  95 act gga aca acc ttt ggc aat gag att gtg tgt tac gaa aat cca agt       336
        Thr Gly Thr Thr Phe Gly Asn Glu Ile Val Cys Tyr Glu Asn Pro Ser
                        100                         105                 110 ccc act gca gga att cat cgt gtc gtg ttt ata ttg ttt cga cag ctt       384
        Pro Thr Ala Gly Ile His Arg Val Val Phe Ile Leu Phe Arg Gln Leu
                115                         120                 125 ggc agg caa aca gtg tat gca cca ggg tgg cgc cag aac ttc aac act       432
        Gly Arg Gln Thr Val Tyr Ala Pro Gly Trp Arg Gln Asn Phe Asn Thr
        130                         135                 140 cgc gag ttt gct gag atc tac aat ctc ggc ctt ccc gtg gcc gca gtt       480
        Arg Glu Phe Ala Glu Ile Tyr Asn Leu Gly Leu Pro Val Ala Ala Val
        145                 150                 155                      160 ttc tac aat tgt cag agg gag agt ggc tgc gga gga aga aga ctt tag       528
        Phe Tyr Asn Cys Gln Arg Glu Ser Gly Cys Gly Gly Arg Arg Leu
                        165                         170                 175

<210> SEQ ID NO 4
        <211> LENGTH: 175
        <212> TYPE: PRT
        <213> ORGANISM: Arabidopsis thaliana

<400> SEQUENCE: 4

Met Ser Ile Asn Ile Arg Asp Pro Leu Ile Val Ser Arg Val Val Gly
        1               5                   10                  15

Asp Val Leu Asp Pro Phe Asn Arg Ser Ile Thr Leu Lys Val Thr Tyr
                        20                  25                  30

Gly Gln Arg Glu Val Thr Asn Gly Leu Asp Leu Arg Pro Ser Gln Val
                35                  40                  45

Gln Asn Lys Pro Arg Val Glu Ile Gly Gly Glu Asp Leu Arg Asn Phe
         50                 55                  60

Tyr Thr Leu Val Met Val Asp Pro Asp Val Pro Ser Pro Ser Asn Pro
        65                  70                  75                  80

His Leu Arg Glu Asn Leu His Trp Leu Val Thr Asp Ile Pro Ala Thr
                        85                  90                  95

Thr Gly Thr Thr Phe Gly Asn Glu Ile Val Cys Tyr Glu Asn Pro Ser
                        100                 105                 110

Pro Thr Ala Gly Ile His Arg Val Val Phe Ile Leu Phe Arg Gln Leu
                115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
        145                 150                 155                 160
```

```
Phe Tyr Asn Cys Gln Arg Glu Ser Gly Cys Gly Gly Arg Leu
            165                 170                 175
```

<210> SEQ ID NO 5
<211> LENGTH: 540
<212> TYPE: DNA
<213> ORGANISM: Oryza sativa
<220> FEATURE:
<221> NAME/KEY: CDS
<222> LOCATION: (1)..(540)

<400> SEQUENCE: 5

```
atg gcc gga agt ggc agg gac agg gac cct ctt gtg gtt ggt agg gtt      48
Met Ala Gly Ser Gly Arg Asp Arg Asp Pro Leu Val Val Gly Arg Val
1               5                   10                  15 gtg ggt gat gtg ctg gac gcg ttc gtc cgg agc acc aac ctc aag gtc      96
Val Gly Asp Val Leu Asp Ala Phe Val Arg Ser Thr Asn Leu Lys Val
                20                  25                  30 acc tat ggc tcc aag acc gtg tcc aat ggc tgc gag ctc aag ccg tcc     144
Thr Tyr Gly Ser Lys Thr Val Ser Asn Gly Cys Glu Leu Lys Pro Ser
            35                  40                  45 atg gtc acc cac cag cct agg gtc gag gtc ggc ggc aat gac atg agg     192
Met Val Thr His Gln Pro Arg Val Glu Val Gly Gly Asn Asp Met Arg
        50                  55                  60 aca ttc tac acc ctt gtg atg gta gac cca gat gca cca agc cca agt     240
Thr Phe Tyr Thr Leu Val Met Val Asp Pro Asp Ala Pro Ser Pro Ser
65                  70                  75                  80 gac cct aac ctt agg gag aac cta cat tgg ttg gtc act gat att cct     288
Asp Pro Asn Leu Arg Glu Asn Leu His Trp Leu Val Thr Asp Ile Pro
                85                  90                  95 ggt act act gca gcg tca ttt ggg caa gag gtg atg tgc tac gag agc     336
Gly Thr Thr Ala Ala Ser Phe Gly Gln Glu Val Met Cys Tyr Glu Ser
            100                 105                 110 cca agg cca acc atg ggg atc cac cgg ctg gtg ttc gtg ctg ttc cag     384
Pro Arg Pro Thr Met Gly Ile His Arg Leu Val Phe Val Leu Phe Gln
        115                 120                 125 cag ctg ggg cgt cag aca gtg tac gcg ccc ggg tgg cgt cag aac ttc     432
Gln Leu Gly Arg Gln Thr Val Tyr Ala Pro Gly Trp Arg Gln Asn Phe
    130                 135                 140 aac acc aag gac ttc gcc gag ctc tac aac ctc ggc tcg ccg gtc gcc     480
Asn Thr Lys Asp Phe Ala Glu Leu Tyr Asn Leu Gly Ser Pro Val Ala
145                 150                 155                 160 gcc gtc tac ttc aac tgc cag cgc gag gca ggc tcc ggc ggc agg agg     528
Ala Val Tyr Phe Asn Cys Gln Arg Glu Ala Gly Ser Gly Gly Arg Arg
                165                 170                 175 gtc tac ccc tag                                                      540
Val Tyr Pro
```

<210> SEQ ID NO 6
<211> LENGTH: 179
<212> TYPE: PRT
<213> ORGANISM: Oryza sativa

<400> SEQUENCE: 6

```
Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
                20                  25                  30

Thr Tyr Gly Ser Lys Thr Val Ser Asn Gly Cys Glu Leu Lys Pro Ser
            35                  40                  45
```

Met Val Thr His Gln Pro Arg Val Glu Val Gly Gly Asn Asp Met Arg
50              55                  60

Thr Phe Tyr Thr Leu Val Met Val Asp Pro Asp Ala Pro Ser Pro Ser
65              70                  75                  80

Asp Pro Asn Leu Arg Glu Asn Leu His Trp Leu Val Thr Asp Ile Pro
                85                  90                  95

Gly Thr Thr Ala Ala Ser Phe Gly Gln Glu Val Met Cys Tyr Glu Ser
                100                 105                 110

Pro Arg Pro Thr Met Gly Ile His Arg Leu Val Phe Val Leu Phe Gln
            115                 120                 125

Gln Leu Gly Arg Gln Thr Val Tyr Ala Pro Gly Trp Arg Gln Asn Phe
130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro

<210> SEQ ID NO 7
<211> LENGTH: 175
<212> TYPE: PRT
<213> ORGANISM: Zea mays

<400> SEQUENCE: 7

Met Ser Ala Thr Asp His Leu Val Met Ala Arg Val Ile Gln Asp Val
1               5                   10                  15

Leu Asp Pro Phe Thr Pro Thr Ile Pro Leu Arg Ile Thr Tyr Asn Asn
                20                  25                  30

Arg Leu Leu Leu Pro Ser Ala Glu Leu Lys Pro Ser Ala Val Val Ser
            35                  40                  45

Lys Pro Arg Val Asp Ile Gly Gly Ser Asp Met Arg Ala Phe Tyr Thr
50                  55                  60

Leu Val Leu Ile Asp Pro Asp Ala Pro Ser Pro Ser His Pro Ser Leu
65                  70                  75                  80

Arg Glu Tyr Leu His Trp Met Val Thr Asp Ile Pro Glu Thr Thr Ser
                85                  90                  95

Val Asn Phe Gly Gln Glu Leu Ile Phe Tyr Glu Arg Pro Asp Pro Arg
                100                 105                 110

Ser Gly Ile His Arg Leu Val Phe Val Leu Phe Arg Gln Leu Gly Arg
            115                 120                 125

Gly Thr Val Phe Ala Pro Glu Met Arg His Asn Phe Asn Cys Arg Ser
130                 135                 140

Phe Ala Arg Gln Tyr His Leu Ser Ile Ala Thr Ala Thr Tyr Phe Asn
145                 150                 155                 160

Cys Gln Arg Glu Gly Gly Ser Gly Gly Arg Arg Phe Arg Glu Glu
                165                 170                 175

<210> SEQ ID NO 8
<211> LENGTH: 172
<212> TYPE: PRT
<213> ORGANISM: Glycine max

<400> SEQUENCE: 8

Met Ala Arg Glu Asn Pro Leu Val Ile Gly Gly Val Ile Gly Asp Val
1               5                   10                  15

Leu Asn Pro Phe Thr Ser Ser Val Ser Leu Thr Val Ser Ile Asn Asn

```
                20                  25                  30
Arg Ala Ile Ser Asn Gly Leu Glu Leu Arg Pro Ser Gln Val Val Asn
            35                  40                  45

Arg Pro Arg Val Thr Val Gly Gly Glu Asp Leu Arg Thr Phe Tyr Thr
        50                  55                  60

Leu Val Met Val Asp Ala Asp Ala Pro Ser Pro Ser Asn Pro Val Leu
65                  70                  75                  80

Arg Glu Tyr Leu His Trp Met Val Thr Asp Ile Pro Ala Thr Thr Asn
                85                  90                  95

Ala Ser Phe Gly Arg Glu Val Val Phe Tyr Glu Ser Pro Asn Pro Ser
            100                 105                 110

Val Gly Ile His Arg Ile Val Phe Val Leu Phe Gln Gln Leu Gly Arg
        115                 120                 125

Asp Thr Val Ile Thr Pro Glu Trp Arg His Asn Phe Asn Ser Arg Asn
    130                 135                 140

Phe Ala Glu Ile Asn Asn Leu Ala Pro Val Ala Ala Tyr Ala Asn
145                 150                 155                 160

Cys Gln Arg Glu Arg Gly Cys Gly Gly Arg Arg Tyr
                165                 170
```

<210> SEQ ID NO 9
<211> LENGTH: 175
<212> TYPE: PRT
<213> ORGANISM: Arabidopsis thaliana

<400> SEQUENCE: 9

```
Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 10
<211> LENGTH: 175
<212> TYPE: PRT
<213> ORGANISM: Arabidopsis thaliana

<400> SEQUENCE: 10

Met Ser Leu Ser Arg Arg Asp Pro Leu Val Val Gly Ser Val Val Gly

```
  1               5                  10                 15
Asp Val Leu Asp Pro Phe Thr Arg Leu Val Ser Leu Lys Val Thr Tyr
                20                 25                 30

Gly His Arg Glu Val Thr Asn Gly Leu Asp Leu Arg Pro Ser Gln Val
                35                 40                 45

Leu Asn Lys Pro Ile Val Glu Ile Gly Gly Asp Phe Arg Asn Phe
 50                 55                 60

Tyr Thr Leu Val Met Val Asp Pro Asp Val Pro Ser Pro Ser Asn Pro
 65                 70                 75                 80

His Gln Arg Glu Tyr Leu His Trp Leu Val Thr Asp Ile Pro Ala Thr
                85                 90                 95

Thr Gly Asn Ala Phe Gly Asn Glu Val Val Cys Tyr Glu Ser Pro Arg
                100                105                110

Pro Pro Ser Gly Ile His Arg Ile Val Leu Val Leu Phe Arg Gln Leu
                115                120                125

Gly Arg Gln Thr Val Tyr Ala Pro Gly Trp Arg Gln Gln Phe Asn Thr
                130                135                140

Arg Glu Phe Ala Glu Ile Tyr Asn Leu Gly Leu Pro Val Ala Ala Ser
145                150                155                160

Tyr Phe Asn Cys Gln Arg Glu Asn Gly Cys Gly Gly Arg Arg Thr
                165                170                175
```

<210> SEQ ID NO 11
<211> LENGTH: 176
<212> TYPE: PRT
<213> ORGANISM: Glycine max

<400> SEQUENCE: 11

```
Met Pro Ser Gly Ser Arg Asp Pro Leu Val Gly Gly Val Ile Gly
 1                  5                  10                 15

Asp Val Leu Asp Pro Phe Glu Tyr Ser Ile Pro Met Arg Val Thr Tyr
                20                 25                 30

Asn Asn Arg Asp Val Ser Asn Gly Cys Glu Phe Lys Pro Ser Gln Val
                35                 40                 45

Val Asn Gln Pro Arg Val Asn Ile Gly Gly Asp Asp Leu Arg Asn Phe
 50                 55                 60

Tyr Thr Leu Ile Ala Val Asp Pro Asp Ala Pro Ser Pro Ser Asp Pro
 65                 70                 75                 80

Asn Leu Arg Glu Tyr Leu His Trp Leu Val Thr Asp Ile Pro Ala Thr
                85                 90                 95

Thr Gly Ala Ser Phe Gly His Glu Val Val Thr Tyr Glu Ser Pro Arg
                100                105                110

Pro Met Met Gly Ile His Arg Leu Val Phe Val Leu Phe Arg Gln Leu
                115                120                125

Gly Arg Glu Thr Val Tyr Ala Pro Gly Trp Arg Gln Asn Phe Asn Thr
                130                135                140

Lys Glu Phe Ala Glu Leu Tyr Asn Leu Gly Leu Pro Val Ala Ala Val
145                150                155                160

Tyr Phe Asn Ile Gln Arg Glu Ser Gly Ser Gly Gly Arg Arg Leu Tyr
                165                170                175
```

<210> SEQ ID NO 12
<211> LENGTH: 177
<212> TYPE: PRT
<213> ORGANISM: Solanum lycopersicum

```
<400> SEQUENCE: 12

Met Pro Arg Glu Arg Asp Pro Leu Val Val Gly Arg Val Gly Asp
1               5                   10                  15

Val Leu Asp Pro Phe Thr Arg Thr Ile Gly Leu Arg Val Ile Tyr Arg
            20                  25                  30

Asp Arg Glu Val Asn Asn Gly Cys Glu Leu Arg Pro Ser Gln Val Ile
        35                  40                  45

Asn Gln Pro Arg Val Glu Val Gly Gly Asp Leu Arg Thr Phe Phe
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ser Ser Phe Gly Gln Glu Ile Val Ser Tyr Glu Ser Pro Arg Pro
                100                 105                 110

Ser Met Gly Ile His Arg Phe Val Phe Val Leu Phe Arg Gln Leu Gly
                115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg Ser Ala
                165                 170                 175

Asp

<210> SEQ ID NO 13
<211> LENGTH: 179
<212> TYPE: PRT
<213> ORGANISM: Oryza sativa

<400> SEQUENCE: 13

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
                100                 105                 110

Pro Arg Pro Thr Met Gly Ile His Arg Leu Val Phe Val Leu Phe Gln
                115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro
```

<210> SEQ ID NO 14
<211> LENGTH: 174
<212> TYPE: PRT
<213> ORGANISM: Malus pumila var. domestica

<400> SEQUENCE: 14

Met Pro Arg Asp Arg Asp Pro Leu Val Val Gly Arg Val Gly Asp
1               5                   10                  15

Val Leu Asp Pro Phe Thr Arg Ser Val Ser Leu Arg Val Thr Tyr Gly
            20                  25                  30

Thr Lys Glu Val Asn Asn Gly Cys Glu Leu Lys Pro Ser Glu Val Val
        35                  40                  45

Gln Gln Pro Arg Ala Asp Ile Gly Gly Asp Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

Ala Ala Ser Phe Gly Gln Glu Ile Val Cys Tyr Glu Ser Pro Arg Pro
            100                 105                 110

Thr Val Gly Ile His Arg Phe Val Leu Val Val Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ser Val Val Tyr
145                 150                 155                 160

Phe Asn Cys Gln Arg Glu Gly Gly Ser Gly Gly Arg Arg Arg
                165                 170

<210> SEQ ID NO 15
<211> LENGTH: 60
<212> TYPE: DNA
<213> ORGANISM: Artificial
<220> FEATURE:
<223> OTHER INFORMATION: Synthetic DNA

<400> SEQUENCE: 15
ggggacaagt ttgtacaaaa aagcaggctt catgtctata aatataagag accctcttat      60

<210> SEQ ID NO 16
<211> LENGTH: 60
<212> TYPE: DNA
<213> ORGANISM: Artificial
<220> FEATURE:
<223> OTHER INFORMATION: Synthetic DNA

<400> SEQUENCE: 16
ggggaccact ttgtacaaga aagctgggtt aagtcttctt cctccgcagc cactctccct      60

<210> SEQ ID NO 17
<211> LENGTH: 586
<212> TYPE: DNA
<213> ORGANISM: Artificial
<220> FEATURE:
<223> OTHER INFORMATION: A coding region of AtFT having attB1 and attB2

<400> SEQUENCE: 17
ggggacaagt ttgtacaaaa aagcaggctt catgtctata aatataagag accctcttat      60
agtaagcaga gttgttggag acgttcttga tccgttaat agatcaatca ctctaaaggt     120

```
tacttatggc caaagagagg tgactaatgg cttggatcta aggccttctc aggttcaaaa      180
caagccaaga gttgagattg gtggagaaga cctcaggaac ttctatactt tggttatggt      240
ggatccagat gttccaagtc ctagcaaccc tcacctccga gaatatctcc attggttggt      300
gactgatatc cctgctacaa ctggaacaac ctttggcaat gagattgtgt gttacgaaaa      360
tccaagtccc actgcaggaa ttcatcgtgt cgtgtttata ttgtttcgac agcttggcag      420
gcaaacagtg tatgcaccag gtggcgccaa gaacttcaac actcgcgagt ttgctgagat      480
ctacaatctc ggccttcccg tggccgcagt tttctacaat tgtcagaggg agagtggctg      540
cggaggaaga agacttaacc cagctttctt gtacaaagtg gtcccc                     586
```

<210> SEQ ID NO 18
<211> LENGTH: 601
<212> TYPE: DNA
<213> ORGANISM: Artificial
<220> FEATURE:
<223> OTHER INFORMATION: A coding region of OsHd3a having attB1 and
      attB2

<400> SEQUENCE: 18

```
ggggacaagt ttgtacaaaa aagcaggctc catggccgga agtggcaggg acagggaccc       60
tcttgtggtt ggtagggttg tgggtgatgt gctggacgcg ttcgtccgga gcaccaacct      120
caaggtcacc tatggctcca agaccgtgtc caatggctgc gagctcaagc cgtccatggt      180
cacccaccag cctagggtcg aggtcggcgg caatgacatg aggacattct acacccttgt      240
gatggtagac ccagatgcac caagcccaag tgaccctaac cttagggagt atctacattg      300
gttggtcact gatattcctg gtactactgc agcgtcattt gggcaagagg tgatgtgcta      360
cgagagccca aggccaacca tggggatcca ccggctggtg ttcgtgctgt tccagcagct      420
ggggcgtcag acagtgtacg cgcccgggtg gcgtcagaac ttcaacacca aggacttcgc      480
cgagctctac aacctcggct cgccggtcgc gccgtctac ttcaactgcc agcgcgaggc      540
aggctccggc ggcaggaggg tctacccta ggacccagct ttcttgtaca agtggtccc      600
c                                                                      601
```

<210> SEQ ID NO 19
<211> LENGTH: 26
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (24)..(24)
<223> OTHER INFORMATION: n is inosine

<400> SEQUENCE: 19
ytnmgngart ayytncaytg gytngt                                            26

```
<210> SEQ ID NO 20
<211> LENGTH: 25
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (11)..(11)
<223> OTHER INFORMATION: n is inosine
<220> FEATURE:
<221> NAME/KEY: misc_feature
<222> LOCATION: (17)..(17)
<223> OTHER INFORMATION: n is inosine
<220> FEATURE:
<221> NAME/KEY: misc_feature
<222> LOCATION: (20)..(20)
<223> OTHER INFORMATION: n is inosine
<220> FEATURE:
<221> NAME/KEY: misc_feature
<222> LOCATION: (23)..(23)
<223> OTHER INFORMATION: n is inosine

<400> SEQUENCE: 20
traarttytg nckccanccn ggngc                                          25

<210> SEQ ID NO 21
<211> LENGTH: 23
<212> TYPE: DNA
<213> ORGANISM: Artificial
<220> FEATURE:
<223> OTHER INFORMATION: Synthetic DNA

<400> SEQUENCE: 21
cacccgtcgg tggcccatta ttg                                            23

<210> SEQ ID NO 22
<211> LENGTH: 22
<212> TYPE: DNA
<213> ORGANISM: Artificial
<220> FEATURE:
<223> OTHER INFORMATION: Synthetic DNA

<400> SEQUENCE: 22
tcttatttca cccggatcga gt                                             22

<210> SEQ ID NO 23
<211> LENGTH: 613
<212> TYPE: DNA
<213> ORGANISM: Artificial
<220> FEATURE:
<223> OTHER INFORMATION: A coding region of ScFT3 having cacc sequence

<400> SEQUENCE: 23
cacccgtcgg tggcccatta ttgctgggct ggccgtgatc gaccggcacg cagcagcgca      60
gcagcggcca tgcagcgcgg ggacccgctg gcggtggggc gcatcatcgg cgacgtggtg     120
gaccccttcg tgcgccgggt gccgctccgc gtcgcctacg ccgcgcgcga gatctccaac     180
ggctgcgagc tcaggccctc cgccatcgcc gaccagccgc gcgtcgaggt cggcggaccc     240
gacatgcgca ccttctacac cctcgtgatg gtggatcctg atgcgccaag ccccagcgat     300
cccaacctca gggagtacct gcactggctg gtcactgaca ttccggcgac gactggagtt     360
tcttttggga ctgaggttgt gtgctacgag agcccacggc cggtgctggg aatccacagg     420
atagtgtttc tgctcttcca acagctcggc cggcagacgg tctacgcccc agggtggcgg     480
cagaacttca gcaccgtgga cttcgccgag ctctacaacc tcggcttgcc ggtcgccgct     540
```

```
gtctacttca actgccaaag ggagtccgga actggtggga gaagaatgtg aactcgatcc        600
gggtgaaata aga                                                           613
```

<210> SEQ ID NO 24
<211> LENGTH: 60
<212> TYPE: DNA
<213> ORGANISM: Artificial
<220> FEATURE:
<223> OTHER INFORMATION: Synthetic DNA

<400> SEQUENCE: 24

```
ggggacaagt ttgtacaaaa aagcaggctc catgttcaat atgtctaggg acccattggt        60
```

<210> SEQ ID NO 25
<211> LENGTH: 60
<212> TYPE: DNA
<213> ORGANISM: Artificial
<220> FEATURE:
<223> OTHER INFORMATION: Synthetic DNA

<400> SEQUENCE: 25

```
ggggaccact ttgtacaaga aagctgggtc tcaccttatg taccttcttc caccacagcc        60
```

<210> SEQ ID NO 26
<211> LENGTH: 595
<212> TYPE: DNA
<213> ORGANISM: Artificial
<220> FEATURE:
<223> OTHER INFORMATION: A coding region of ScFT5 having attB1 and attB2

<400> SEQUENCE: 26

```
ggggacaagt ttgtacaaaa aagcaggctc catgttcaat atgtctaggg acccattggt        60
cgtcgggcat gttgtggggg atattgtgga tcccttcatc acaactgcgt cactgagggt       120
gttctacaac aataaggaga tgacaaatgg ttctgagctt aagccatctc aagtaatgaa       180
tgagccaagg gtcccacatca gtgggcgtga catgaggact ctctacacac ttgtcatggt       240
ggacccagat gcaccaagcc ccagtaaccc tactaaaaga gagaaccttc actggttggt       300
gacagacatt ccagagacaa ctgatgccag cttcggaat gagatagttc cttatgagag       360
cccacgtcca actgccggaa tccatcgctt tgcattcgtc ttgttcaggc agtcagtcag       420
gcagactacc tatgcgccgg ggtggagatc aaactttaac accagggact cgcagccat        480 ctacaacctt ggctcccctg tcgctgcagt gtacttcaac tgccagagag agaacggctg       540
tggtggaaga aggtacataa ggtgagaccc agctttcttg tacaaagtgg tcccc           595
```

<210> SEQ ID NO 27
<211> LENGTH: 589
<212> TYPE: DNA
<213> ORGANISM: Artificial
<220> FEATURE:
<223> OTHER INFORMATION: A coding region of a mutant AtFT having Y85N
      mutant

<400> SEQUENCE: 27

```
ggggacaagt ttgtacaaaa aagcaggctc catgtctata aatataagag accctcttat        60
agtaagcaga gttgttggag acgttcttga tccgtttaat agatcaatca ctctaaaggt       120
tacttatggc caaagagagg tgactaatgg cttggatcta aggccttctc aggttcaaaa       180
caagccaaga gttgagattg gtggagaaga cctcaggaac ttctatactt tggttatggt       240
ggatccagat gttccaagtc ctagcaaccc tcacctccga gaaacctcc attggttggt        300
```

```
gactgatatc cctgctacaa ctggaacaac ctttggcaat gagattgtgt gttacgaaaa    360
tccaagtccc actgcaggaa ttcatcgtgt cgtgtttata ttgtttcgac agcttggcag    420
gcaaacagtg tatgcaccag ggtggcgcca gaacttcaac actcgcgagt ttgctgagat    480
ctacaatctc ggccttcccg tggccgcagt tttctacaat tgtcagaggg agagtggctg    540
cggaggaaga agactttagg acccagcttt cttgtacaaa gtggtcccc                589

<210> SEQ ID NO 28
<211> LENGTH: 601
<212> TYPE: DNA
<213> ORGANISM: Artificial
<220> FEATURE:
<223> OTHER INFORMATION: A coding region of a mutant OsHd3a having Y87N
      mutant

<400> SEQUENCE: 28
ggggacaagt ttgtacaaaa aagcaggctc catggccgga agtggcaggg acagggaccc     60
tcttgtggtt ggtagggttg tgggtgatgt gctggacgcg ttcgtccgga gcaccaacct    120
caaggtcacc tatggctcca agaccgtgtc caatggctgc gagctcaagc cgtccatggt    180
cacccaccag cctagggtcg aggtcggcgg caatgacatg aggacattct acacccttgt    240
gatggtagac ccagatgcac caagcccaag tgaccctaac cttagggaga acctacattg    300
gttggtcact gatattcctg gtactactgc agcgtcattt gggcaagagg tgatgtgcta    360
cgagagccca aggccaacca tggggatcca ccggctggtg ttcgtgctgt tccagcagct    420
ggggcgtcag acagtgtacg cgcccggtg gcgtcagaac ttcaacacca aggacttcgc    480
cgagctctac aacctcggct cgccggtcgc cgccgtctac ttcaactgcc agcgcgaggc    540
aggctccggc ggcaggaggg tctaccccta ggacccagct ttcttgtaca aagtggtccc    600
c                                                                   601
```